(12) United States Patent
Halvorsen

(10) Patent No.: US 11,166,855 B2
(45) Date of Patent: Nov. 9, 2021

(54) DIAPER SENSOR DEVICE, METHOD AND SYSTEM FOR DIAPER SURVEILLANCE

(71) Applicant: SENSCOM AS, Oslo (NO)

(72) Inventor: Vidar Rinde Halvorsen, Oslo (NO)

(73) Assignee: SensCom AS

( * ) Notice: Subject to any disclaimer, the term of this patent is extended or adjusted under 35 U.S.C. 154(b) by 162 days.

(21) Appl. No.: 16/309,316

(22) PCT Filed: Feb. 21, 2017

(86) PCT No.: PCT/NO2017/000006
§ 371 (c)(1),
(2) Date: Dec. 12, 2018

(87) PCT Pub. No.: WO2017/217859
PCT Pub. Date: Dec. 21, 2017

(65) Prior Publication Data
US 2019/0314214 A1    Oct. 17, 2019

(30) Foreign Application Priority Data

Jun. 17, 2016   (NO) .................................. 20161024

(51) Int. Cl.
*A61F 13/42*   (2006.01)
*A61F 13/84*   (2006.01)

(52) U.S. Cl.
CPC ........ *A61F 13/42* (2013.01); *A61F 2013/421* (2013.01); *A61F 2013/424* (2013.01); *A61F 2013/8482* (2013.01)

(58) Field of Classification Search
CPC ................ A61F 13/42; A61F 2013/421; A61F 2013/424; A61F 2013/8482;

(Continued)

(56) References Cited

U.S. PATENT DOCUMENTS 6,097,297 A     8/2000  Fard
7,250,547 B1    7/2007  Hofmeister et al.
(Continued)

FOREIGN PATENT DOCUMENTS

CN    104398343 A    3/2015
CN    104783965 A    7/2015
(Continued)

OTHER PUBLICATIONS

International Bureau, International Search Report and Written Opinion in International Application No. PCT/NO2017/000006, dated Dec. 7, 2017.

*Primary Examiner* — Tatyana Zalukaeva
*Assistant Examiner* — Jessica R Arble
(74) *Attorney, Agent, or Firm* — KPPB LLP

(57) ABSTRACT

The invention comprises a diaper sensor device comprising at least two sensor units each comprising at least a temperature sensor and a humidity sensor; optionally a positional sensor; a microcontroller communicating with the sensors and comprising a transmitter for transmitting data from the sensors; a power unit supplying power to the sensors, the microcontroller and the transmitter; a flexible watertight casing; housing the sensors, the transmitter; and the power unit, and fastening means for fastening the diaper sensor device on the outside of the diaper.

Furthermore the invention comprises a method and a system for determining the existence and class of human excreta in a diaper.

2 Claims, 3 Drawing Sheets

(58) Field of Classification Search
CPC .... A61F 2013/1513; A61F 2013/15146; A61F 2013/15154
See application file for complete search history.

(56) References Cited

U.S. PATENT DOCUMENTS

| | | |
|---|---|---|
| 2005/0156744 A1 | 7/2005 | Pires |
| 2005/0195085 A1 | 9/2005 | Cretu-Petra |
| 2009/0326417 A1 | 12/2009 | Ales, III et al. |
| 2012/0116337 A1 | 5/2012 | Ales et al. |
| 2012/0245542 A1* | 9/2012 | Suzuki ................ A61F 13/42 604/319 |
| 2012/0310191 A1* | 12/2012 | LaVon ............ A61F 13/51401 604/361 |
| 2013/0303867 A1 | 11/2013 | Elfstrom et al. |
| 2015/0223755 A1 | 8/2015 | Abir |
| 2015/0257942 A1* | 9/2015 | Kim ..................... G08B 25/10 604/361 |
| 2016/0095758 A1 | 4/2016 | Haire et al. |
| 2016/0310329 A1* | 10/2016 | Patel ..................... A61B 5/1116 |
| 2017/0252225 A1* | 9/2017 | Arizti ..................... A61F 13/49 |
| 2018/0333306 A1* | 11/2018 | Ahong ................. A61B 5/6843 |

FOREIGN PATENT DOCUMENTS

| | | |
|---|---|---|
| JP | 2015-147022 A | 8/2015 |
| WO | WO 2013/061181 A1 | 5/2013 |

* cited by examiner

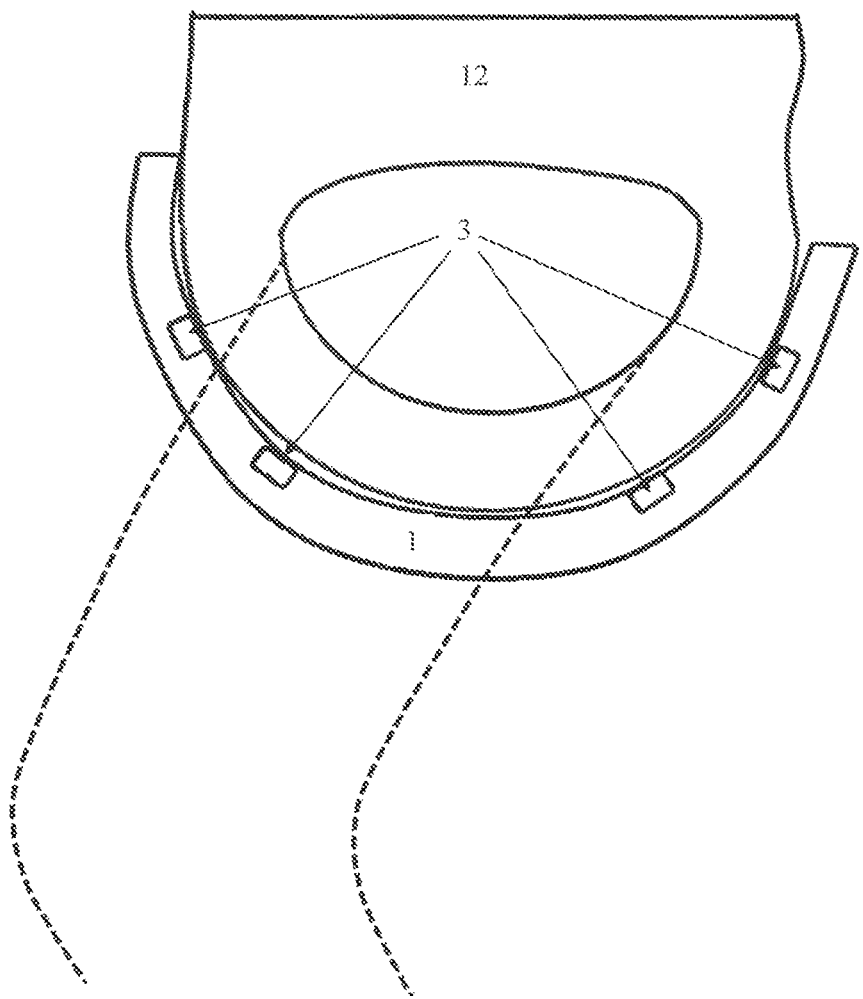

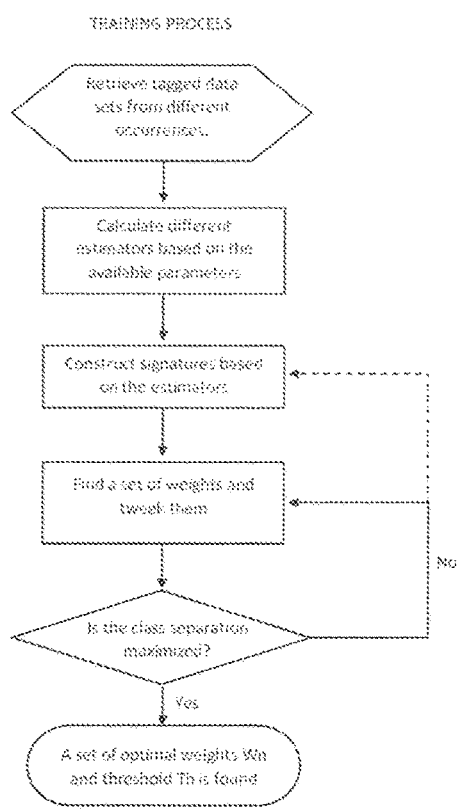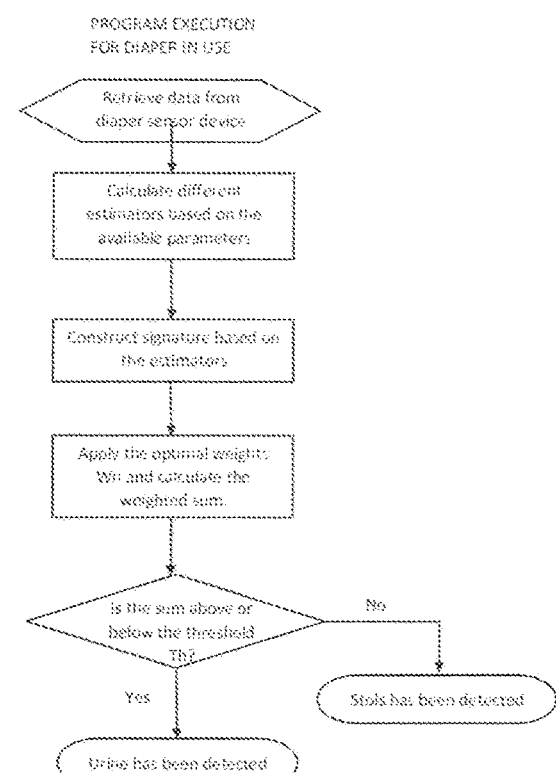

DIAPER SENSOR DEVICE, METHOD AND SYSTEM FOR DIAPER SURVEILLANCE

CROSS-REFERENCE TO RELATED APPLICATIONS

This patent application is the U.S. National Stage of International Patent Application No. PCT/NO2017/000006, filed Feb. 21, 2017, which claims the benefit of Norwegian Patent Application No. 20161024, filed Jun. 17, 2016, which are each incorporated by reference.

FIELD OF INVENTION

The invention relates to diapers and how to avoid negative effects of not changing diapers in time. More specifically it offers a diaper sensor device, method and system for determining the content of the diaper and reporting it to caregiver.

BACKGROUND

Worldwide over 200 million people suffer of incontinence due to age, illness or disability, and the figure is rising in line with the demographics of the population. Globally, it is estimated that approximately 380 million diapers are changed every day on children aged 0-3 years. In Japan the sales of diapers for elderly has passed the sales of diapers for children.

The device and method according to this invention is developed based on a vision of welfare by using a technological sensor solution. The sensors will quickly detect and accurately record the humidity and temperature in the diaper and indicate when the diaper should be changed. It ensures that the diaper is changed at the right time—neither too early nor too late. The effect will be that the diaper only is checked/changed when necessary. Thus, the change of diaper represents a minimum level of disturbance to the user (children/elderly). For parents it will be easier to handle the busy everyday life when the diaper only is changed when it actually needs replacing.

The human skin is not able to withstand the acidic nature of feces. Feces in combination with urine form ammonium inside the diaper. One of the advantages of this invention is that it distinguishes between urine and feces. This enables the person (caregiver) who is supposed to change the diaper on the child or patient to prioritize: If the diaper contains urine it should be changed within a reasonable time. If the diaper contains feces it should be changed immediately.

The positive health effect of proper changing of diapers is enormous in a global perspective. It will reduce the likelihood of infections, eczema and soreness of the bum. Use of drugs/creams and visits to the doctor will also be reduced. In many cases the wounds resulting from acidic feces remaining in contact with skin over a longer period of time will result in use of antibiotics, parents staying away from work because of sick children, great pain for the victim/patient, loss of dignity, permanent scarring and even death in some cases.

Furthermore institutions taking care of incontinent patients using diapers will be able to free time spent on checking diapers. The cost of care will go down and staff can use the saved time on other tasks. In a HMS perspective the number of lifts and transfers of patients will be reduced taking some of the burden away from the backs of the nursing staff. Also the dignity of the patient is upheld by avoiding situations where the patient is sitting/lying in his/her own feces for a longer period of time. The invention can free resources and provide better conditions for both residents, staff, families and institutions.

A number of previous attempts to solve some of these problems should be mentioned. US 20050195085 A1 describe a self-contained, reusable sensing device attached to a diaper, comprising conductivity sensors (SI, S2, S3 and S4), a capacitive sensor (CS), a motion sensor (MS), a microphone (MIC) and a temperature sensor (TS). The output of each said sensors is analyzed by a microcontroller (MC1). Said microcontroller output enters a wireless transmitter, which relays to a remotely monitored pager. Pager display shows visually and by sound the stream of data coming from said pager wireless receiver.

US 20090326417 describes how monitoring the status of an absorbent article can be desirable to various users in various situations. A monitoring device for use with an absorbent article is provided. The monitoring device includes a sensing device and a signaling device. The sensing device is configured to sense a physiological indication related to the absorbent article wearer. The functionality of the monitoring device may be updateable, for instance, by utilizing firmware updates, hardware or user interface changes, software installations, etc. Thus, the monitoring device of the present invention may be utilized over an entire lifespan from infants to elderly without the need for costly replacement or installation of an entirely new monitoring system.

U.S. Pat. No. 6,097,297 A describes a moisture detection system which provides a disposable wicked dual electrode strip as a sensor wick and conductor assembly which can be used in conjunction with any type of diaper or garment. The dual electrode strip includes two conductive strips which have a wick located in contact with the conductive strips. Even a small amount of urine is absorbed by the wick and distributed between the conductive strips to quickly change the resistance between the strips. A detector/transmitter engages the sensor wick and conductor assembly, and can use the sensor wick and conductor assembly as a transmitting antenna for increased range at low power, to alert a receiver carried by a care giver.

US 20120116337 A1 describes absorbent articles and signaling devices for use therewith. The signaling device includes one or more non-invasive sensors configured to detect the presence of a substance, such as a body fluid, in the absorbent article. The signaling device can provide an audible and/or visible alert to the user of the absorbent article when it detects the presence of a substance. The absorbent article includes one or more identifiable characteristics the presence of which pennits operation of the signaling device. In this manner, the present disclosure provides for product and signaling device matching for use.

US 20050156744 A1 describes how a monitoring system identifies a wet diaper by embedding an inexpensive disposable passive humidity sensor, which may be formed of conductive ink, and attaching to the outside of the diaper a detachable transmitting module that is triggered into transmission by the humidity sensor. The transmitting module is sealed and transferable from the wet diaper to a dry one. Uniquely coded data is wirelessly transmitted to a remote receiver. The receiver may be a battery powered portable unit carried by the baby's guardian. In a day care center a multiple function receiver can identify any of several diapers. In hospitals, several strategically located receivers are each capable of recognizing and reporting any wet diaper within its range to a central computer. Low cost and long range are achieved by using a detachable and transportable active transmitter that is not discarded with the wet diaper and therefore can be re-used. False transmissions are prevented by a confirmatory resistance.

U.S. Pat. No. 7,250,547 B1 describes a wetness monitoring system that includes a data collection device that sends wetness measurement data to a central computer that detects changes in wetness measurement data caused by the presence of urine or other dielectric fluids. The data collection device includes a semi-reusable sensor and reusable data collector that are worn on a garment of the person.

WO 2013061181 A1 describes an electronic discriminating device incorporating a non-contact electronic sensor array, a controller, and a signaling device that may indicate the presence of urine and/or bowel movement is disclosed. In particular, the electronic discriminating device can discriminate between an insult of urine only and an insult containing bowel movement. The device can then generate different alerts based on the type of insult. The electronic discriminating device may also emit a signal at or near the opening of an absorbent article or transmit the alert wirelessly to a radio computer device, or smartphone.

US 20160095758 disclose an incontinence detection device and system.

SUMMARY OF THE INVENTION

The invention comprises a diaper sensor device comprising; a microcontroller communicating with the sensors, wherein the microcontroller comprises a transmitter for transmitting data from the sensors; a power unit supplying power to the sensors, the microcontroller and the transmitter. Furthermore the device comprises at least two sensor units each comprising at least a temperature sensor and a humidity sensor; a flexible watertight and machine washable casing, housing the sensors, the transmitter, and the power unit, and fastening means for fastening a diaper sensor device on the outside of the diaper.

Also the invention comprises a method for diaper surveillance, wherein the method comprises the following steps: a) fastening the diaper sensor to the outside of the diaper mainly along the longitudinal centerline of the diaper; b) sensing temperature and humidity at locations along the centerline of the diaper; c) optionally sensing position of the diaper in relation to gravity; d) sending data from the sensors to the processing unit; e) determining the existence and class of human excreta in the diaper based on data received from the diaper sensor device; and f) alerting a caregiver of the determination result.

The device and method according to the invention is combined in a system for diaper surveillance, wherein the system comprises: a diaper sensor device according to claim; a processor connected to a user interface; a memory storing a computer executable program which is able to perform the step e of the method according to claim 8; a receiver connected to the processor and/or memory receiving data sent from the diaper sensor device, wherein the processor determines the existence and class of human excreta in the diaper based on data received from the diaper sensor device.

SHORT DESCRIPTION OF FIGURES

For a better understanding of the invention, and to show how embodiments of the invention may be used, reference will now be made, by way of example, to the accompanying diagrammatic drawings in which:

FIG. 3 shows a diagram of the system.

FIG. 4*a* shows a flow diagram for a training process for establishing a threshold and optimal weights for the estimators.

FIG. 4*b* shows a flow diagram for a program execution for a diaper in use.

DETAILED DESCRIPTION

Figure 1:
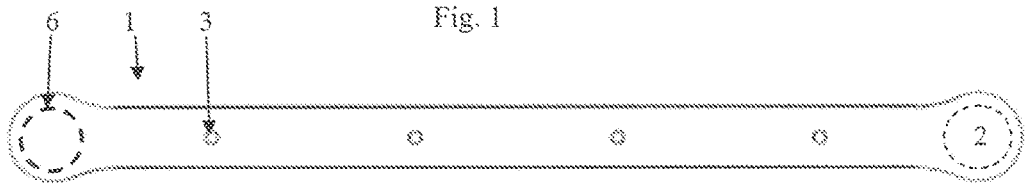
FIG. 1 shows a diaper sensor device and its casing.
Figure 2:
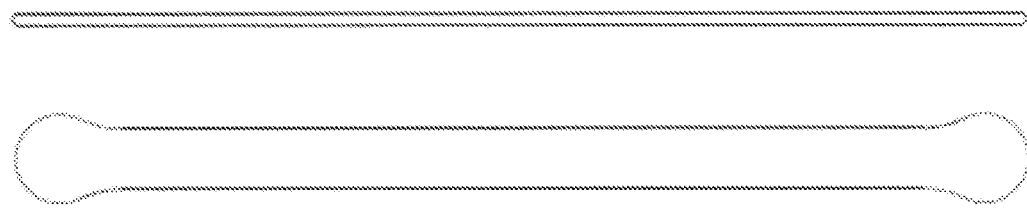
FIG. 2 shows a diaper sensor device attached to a diaper on a user.
Figure 2:
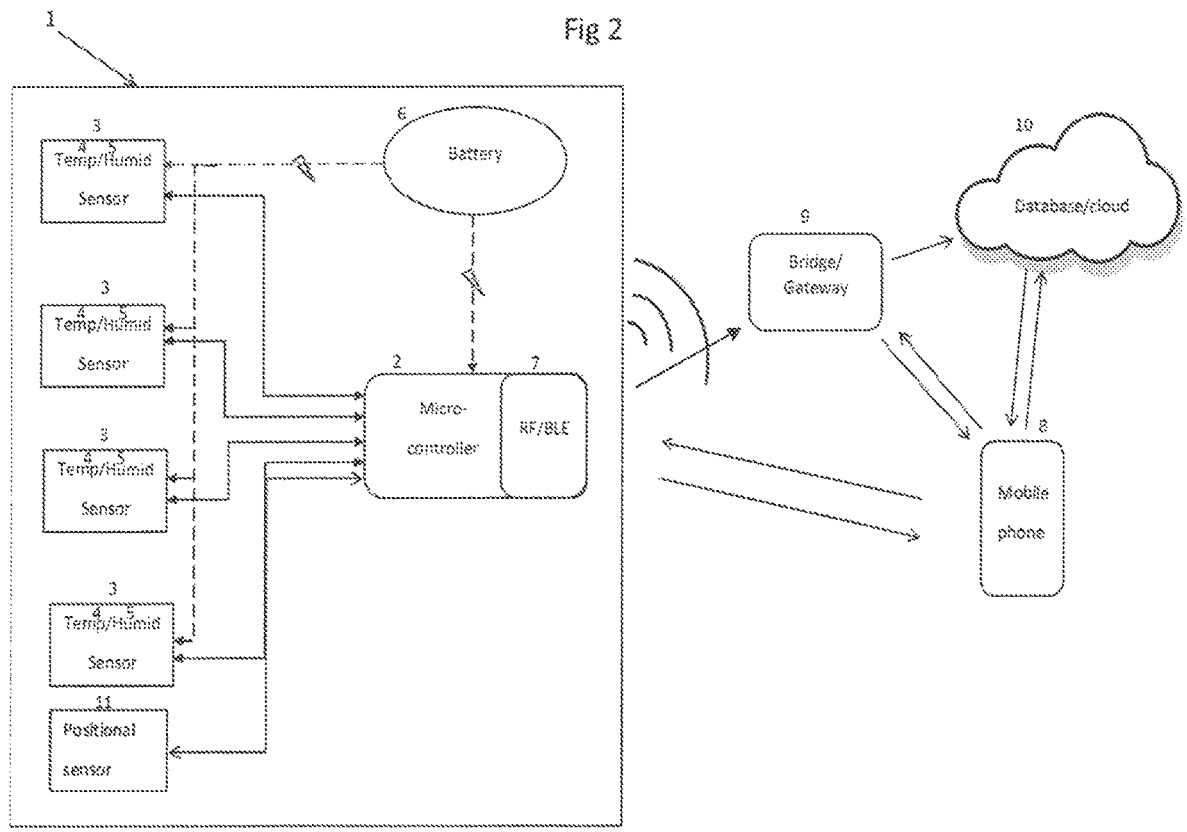

The diaper sensor device 1 shown in FIGS. 1, 2 and 3 is based on a microcontroller 2 communicating with at least two sensor units 3 each comprising at least a temperature sensor 4 and a humidity sensor 5. By using low power components and controlling these, the device can be run for a year on a small coin size battery 6. A minimum of processing should be done in the microcontroller 2 in order to prolong the life span of the power source 6 in the diaper sensor device 1. For the same purpose the diaper sensor device is in a rest modus until the sensors detect a rise in temperature or humidity, most likely due to urine or feces from the user of the diaper. The electronics is casted into a casing 13 of silicon, rubber or plastic to ensure that the device 1 is flexible and waterproof. The diaper sensor device 1 in its casing 13 is shown from three sides in FIG. 1. In fact, it should be machine washable up to 85 degrees for at least 30 minutes. Thus, it complies with the need for keeping it clean and hygienic and meets the requirements set down by health authorities and institutions.

FIG. 2 shows a system for determining existence and class of human excreta in diaper 12 comprising the mentioned diaper sensor device 1. Further essential constituents of the system is a processor connected to a user interface, for instance a mobile phone 8; a memory storing a program which is able to perform the steps of the method according to claim 8 and wherein the program is executable by the mentioned processor; a receiver receiving data sent from the diaper sensor device and being connected to the processor and/or memory. Obviously the processor, the memory and user interface may be integrated in one or more units and take different forms, one of which is shown in FIG. 2. In order to transmit the current status of the diaper sensor device 1, the microcontroller 2 comprises a transmitter 7 i.e. a Bluetooth Low Energy (BLE) RF-module. Depending on the end user, this information can be sent to a mobile unit 8 or via a bridge/gateway 9 to a database 10 in a memory i.e. the cloud. In the latter case, the diaper sensor device 1 can be said to be an Internet of Things (IoT) device. Either way, the information can be sent to notify a caregiver on a mobile unit 8 by using an app. However, sending the information to the cloud 10 will make it possible to use the information in larger administrative systems.

FIG. 3 shows the diaper sensor device being fastened to the outside of a diaper 12 worn by a person with the sensors pointing inward. The way the diaper sensor device 1 is designed and attached to a diaper 12, will make it possible to establish a method in order to classify the content of the diaper 12. The diaper sensor device 1 should be fastened to the outside of the diaper mainly along the longitudinal centerline of the diaper 12. The sensor units 3 in the diaper sensor device 1 are preferably positioned in a mainly straight line for sensing temperature and humidity at locations along the centerline of the diaper. Alternatively the diaper sensor is symmetrically distributed in relation to the centerline of the diaper sensor device 1 and within the limits of the absorbing part of the diaper 12. The number of sensors and the way they are spread out, will contribute to information that can be used for determining the content of the diaper 12. Optionally the diaper sensor device 1 comprises a positional sensor 11 that determines the direction of gravity in relation to the diaper sensor device 1 in order to improve the interpretation of the data. This is because urine will be affected differently by gravity than feces. In one embodiment the positional sensor is a gyroscope sensor.

Normally the microcontroller is in a rest mode, but it sends data from the sensors to the processing unit, if there is a rise in temperature or humidity, then the processing unit determines the existence and class of human excreta in the diaper (12) based on data received from the diaper sensor device (1), and finally alerts the caregiver of the result and finally removing the diaper sensor device (1) from the diaper (12) for further use when disposing the used diaper.

Because the sensors are localized outside the diaper, the diaper itself will act like a filter on the detection of the variables. We actually measure how the content is absorbed by the diaper 12 over a given time interval. As urine and feces have different characteristics, the diaper 12 will absorb these differently. Urine will be quickly absorbed into the diaper and give a quicker response in the sensors compared to feces which to a lesser degree will be absorbed into the diaper 12. Preferably the diaper sensor device 1 is fastened to the diaper 12 by a strip of tape with sufficient length and width to fasten the diaper sensor device 1 to the diaper 12. Alternatively the diaper sensor device 1 is provided with a VELCRO® fastener. In another embodiment the diaper 12 is provided with a pocket into which the diaper sensor device 1 can be inserted.

From the sensors we have 4 parameters; time, position, humidity and temperature. Using these to construct a signature, the processing unit is able to classify the content of the diaper with a given certainty. The signature of each class of human excreta will comprise a weighted sum of estimators based on the four parameters. FIG. 4a shows a training process for obtaining optimal weighting. A tagged set of data is the basis for the training process. A tagged set of data is obtained by caregivers noting the actual presence of urine and feces in the diaper associated with measurements. Then the different estimators will be calculated for each parameter and signatures for each class of human excreta will be constructed based on the estimators. The objective of the training is to maximize the separation between the two classes representing urine and feces. To achieve this, a set of weights is given to the estimators and the weights are adjusted until the class separation is maximized. An estimate of the success rate of the classification algorithm can be obtained by running the algorithm with another set of recordings different from the training set. In practice, the algorithm will input the four parameters and use these to construct a signature. The signature consists of a weighted sum of statistical measures based on the parameters. Simply, by thresholding this result, it is possible to determine whether the content is feces or urine. Alternatively more than one threshold might be used to further differentiate the properties of the human excreta.

When the thresholds have been established the diaper sensor device 1 and corresponding system are ready for use and may be sold to users/caregivers. FIG. 4a shows a possible flow diagram of a program for classifying human excreta. More than one threshold might also be used to further differentiate for quantity of human excreta, the combination of both classes or other properties.

Most diapers on the market will have different characteristics, and users have different sizes and different digestive systems causing different patterns of excretion. The software will be able to offer different settings that enable the caregiver to adapt the system to the needs of the user.

In one embodiment the interpretation and classification of the data can be left to the caregiver simply by displaying the percentage of humidity and the temperature in the different sensors as positioned on the body. A simplification of FIG. 3 with humidity and temperature data displayed as colors close to the corresponding sensors could be imagined.

It should be noted that the described embodiments is examples only and that numerous variations and combinations are possible, which are not described specifically here, but still fall within the scope of the independent claims which defines the invention.

The invention claimed is:

1. A system for diaper surveillance for determining existence and class of human excreta in a diaper comprising:
    a diaper sensor device comprising:
        at least two sensor units each comprising at least a temperature sensor and a humidity sensor,
        a positional sensor,
        a microcontroller communicating with the at least two sensor units and comprising a transmitter for transmitting data from the at least two sensor units,
        a battery supplying power to the at least two sensor units, the microcontroller and the transmitter,
        a flexible casing made of silicon, rubber, or plastic to ensure that the diaper sensor device is waterproof and machine washable, wherein the at least two sensor units, the microcontroller, the transmitter, and the battery are casted into the flexible casing,
    a processor connected to a user interface,
    a memory storing a computer executable program which is able to determine the existence and class of human excreta in the diaper based on data received from the diaper sensor device, wherein the class of human excreta is determined at least partially by diaper orientation data obtained from the positional sensor with respect to the location of the humidity sensor,
    a receiver connected to the processor and/or memory receiving data sent from the diaper sensor device,
    wherein the at least two sensor units are positioned in a mainly straight line, and,
    a strip of tape with sufficient length and width for fastening the diaper sensor device on an outside of the diaper, such that the at least two sensor units are positioned along a longitudinal centerline of the diaper with the at least two sensors pointing inward.

2. The system of claim 1, wherein the diaper orientation data comprises angular orientation of the diaper.

* * * * *